(12) United States Patent
O'Lenick

(10) Patent No.: US 8,680,225 B1
(45) Date of Patent: Mar. 25, 2014

(54) TERMINAL SILICONE POLYGLYCEROL POLYESTERS

(71) Applicant: Thomas George O'Lenick, Dacula, GA (US)

(72) Inventor: Thomas George O'Lenick, Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 0 days.

(21) Appl. No.: 13/986,022

(22) Filed: Mar. 25, 2013

Related U.S. Application Data

(63) Continuation-in-part of application No. 13/506,163, filed on Apr. 2, 2012, now Pat. No. 8,465,730.

(51) Int. Cl.
*C08G 77/46* (2006.01)

(52) U.S. Cl.
USPC ............... 528/29; 528/25; 528/26; 528/31

(58) Field of Classification Search
None
See application file for complete search history.

(56) References Cited

U.S. PATENT DOCUMENTS

| | | | | |
|---|---|---|---|---|
| 4,431,789 | A * | 2/1984 | Okazaki et al. | 528/15 |
| 5,475,125 | A * | 12/1995 | O'Lenick, Jr. | 556/437 |
| 7,084,215 | B2 * | 8/2006 | Dietz et al. | 525/474 |
| 7,638,116 | B2 | 12/2009 | LaVay | |
| 2005/0008600 | A1 * | 1/2005 | Nakanishi et al. | 424/70.12 |
| 2010/0196304 | A1 * | 8/2010 | LaVay et al. | 424/70.12 |

* cited by examiner

*Primary Examiner* — Marc Zimmer

(57) ABSTRACT

The present invention is directed toward a series of polyglycerol polyesters that have silicone terminal groups with tunable ascetics and performance in cosmetic formulation. These novel silicone containing polyglycerol polyesters are designed to be multidimensional. Multidimensional is meant that the polymer contains a variety of groups containing different chemical and physical properties covalently bonded together. The physical properties of the current invention can be tuned rapidly by controlling the ratio of fatty groups, as well as the cross-linker used. Tuned here is meant the ability to adjust the physical properties to a desired value. The resulting polyglycerol polyesters have outstanding aesthetics and physical properties.

11 Claims, No Drawings

TERMINAL SILICONE POLYGLYCEROL POLYESTERS

RELATED APPLICATIONS

This application is a continuation in part of co-pending application Ser. No. 13/506,163 filed Apr. 2, 2012.

FIELD OF THE INVENTION

The present invention is directed toward a series of polyglycerol polyesters that have silicone terminal groups with tunable ascetics and performance in cosmetic formulation. These novel silicone containing polyglycerol polyesters are designed to be multidimensional. Multidimensional is meant that the polymer contains a variety of groups containing different chemical and physical properties covalently bonded together including water loving (hydrophilic), oil loving (oleophilic) and silicone loving groups (siliphilic) groups. The physical properties of the current invention can be tuned rapidly by controlling the ratio of fatty groups, as well as the cross-linker used. Tuned here is meant the ability to adjust the physical properties to a desired value. The resulting polyglycerol polyesters have outstanding aesthetics and physical properties.

These polymers have been designed to be "epigenomic friendly polymers". By "epigenomic friendly polymers" is meant polymers that are designed to have the desired functionality, regiospecifically located either within the polymer or at the external portions, and have molecular weights above 1,500 mwu (daltons) so as to minimize penetration into the skin. It is becoming better and better recognized that low molecular weight, non-polymeric products applied to the skin can penetrate and either up regulate or down regulate genes that can cause unintended consequences. An example is reported by deFlora et al in at http://www.ncbi.nlm.nih.gov/pubmed/21536718. It states, "Among endocrine disruptors, the xenoestrogen bisphenol A (BPA) deserves particular attention due to widespread human exposure. Besides hormonal effects, BPA has been suspected to be involved in breast and prostate carcinogenesis, which share similar estrogen-related mechanisms". There are numerous other examples of lower molecular weight non-proteins causing unintended consequences after penetrating the skin. "Epigenomic friendly polymers" are too large to penetrate.

BACKGROUND OF THE INVENTION

Polyglycerol compounds are well known materials. They are made by the condensation reaction of glycerin. The resulting products are polar and posses several un-reacted hydroxyl groups. The number of glycerin molecules condensed in the reaction is referred to as the degree of polymerization (DP). The condensation reaction run between two glycerin molecules produces water as a byproduct. U.S. Pat. No. 5,721,305 issued Feb. 24, 1998 to Eshuis, et al. entitled Polyglycerol production teaches how polyglycerol is made.

U.S. Pat. No. 3,936,391 issued Feb. 3, 1976 to Gabby entitled "Hydrated polyglycerol Ester Composition" teaches a polyglycerol ester emulsifier is prepared by heating a polyglycerol ester containing 3 to 10 glycerol units and a 1 to 2 saturated fatty acyl ester groups containing 16 to 20 carbon atoms, glycerol and water at a temperature of 125 to 135° F. The heat is maintained until a homogeneous paste-like consistency is imparted thereto.

U.S. Pat. No. 5,674,475 issued Oct. 7, 1997 to Dahms entitled "Emulsifier Composition based on Polyglycerol Ester" teaches an emulsifier composition of a mixture of polyglycerol fatty acid esters and the lactylate of a fatty acid or its salt. This emulsifier is used to manufacture a wide range of different oil in water emulsions.

U.S. Pat. No. 1,424,137 issued July 1922 to Weisberg, entitled "Polyglycerol Resins" discloses a polyglycerol ester of an aromatic dibasic acid used in shellac. This patent, imported herein by reference, addresses solid resins made in solvent. While lacking the critical control of cross-linking and producing a hard rather than a soft ester, this patent shows the state of the art in resins.

Still another U.S. Pat. No. 7,638,116, issued Dec. 29, 2009 by LaVay et al. entitled "Polyglycerol dimer polyester resins" discloses a polyglycerol dimer resin of a polyglycerol containing 3 to 10 repeat units cross-linked by dimer acid. While lacking the critical control of cross-linking and functionalization by fatty groups, this patent shows the state of the art of polyglycerol dimer polyesters.

THE INVENTION

Object of the Invention

The current invention is directed toward a series of multidomain silicone terminated polyglycerol polyesters that are synthesized by the reaction of polyglycerol, a diacid, fatty acid and monofunctional chain capping silicone compound. These multidimensional polyglycerol polyesters contain a mixture of fatty groups with differing melt points. The multidomain nature of the current invention will provide very unique physical properties and ascetics in cosmetic formulations.

Another object of the present invention is to provide a series of products having differing amounts of hydrophilic (polyglycerin derived), oleophilic (fatty) and siliphilic (silicone loving) portions to maximize the ability to formulate personal care products with all three ingredients present.

Other objectives will become clear by reading the specifications. All temperatures are in degrees centigrade, all percentages are percentages by weight, and all patents referenced herein are incorporated herein by reference.

SUMMARY OF THE INVENTION

The present invention is related to a series of novel terminal silicone containing polyglycerol polyesters that are prepared by the reaction of a mixture of fatty acids, polyglycerol and a diacid. The nature of a polymer that contains different physical properties mainly the difference between the water loving nature of polyglycerol and the physical properties of the fatty group and most importantly the terminal silicone produces products that have extremely unique properties. The selection of the fatty groups, the diacid, polyglycerol, and silicone group will drastically change the physical and cosmetic aesthetics of the resulting material.

The compounds of the present invention are made by the esterification reaction of a diacid, polyglycerol, and a mixture of fatty acids and a monofunctional silicone. The resulting products have the compatibility over those materials lacking the combination of these groups. This combination of groups results in a high efficient deposition of the skin, hair and fibers.

DETAILED DESCRIPTION OF THE INVENTION

The present invention is aimed at a series of novel silicone terminated polyglycerol polyester that provides desired aesthetics and structure in cosmetic formulations.

Polyglycerol Polyester

A terminal silicone polyester having the following structure:

$$\left[ R^1(O)C \begin{matrix} OC(O)R^1 \\ OC(O)R^2 \\ O \\ O \\ O \\ O \\ OC(O)R^1 \\ O \\ O \\ OC(O)R^2 \\ OC(O)R^2 \end{matrix} \right]_n \left[ \begin{matrix} OC(O)R^1 \\ O \\ O \\ O \\ O \\ R^3 \\ O \\ O \\ OC(O)R^2 \\ OC(O)R^1 \end{matrix} \right]_x$$

wherein, $R^1$ is $$CH_3-Si(CH_3)_2-(O-Si(CH_3)_2)_a-(O-Si(CH_3)((CH_2)_{10}-))-O-Si(CH_3)_3$$

a is an integer ranging from 1 to 20;

$R^2$ is selected from the group consisting of $$CH_3-Si(CH_3)_2-(O-Si(CH_3)_2)_a-(O-Si(CH_3)((CH_2)_{10}-))-O-Si(CH_3)_3$$

a is an integer ranging from 1 to 20;

and alkyl containing 8 to 26 carbons or mixtures thereof;

$R^3$ is independently selected from the group consisting of alkyl having 2 to 12 carbons, alkyl having the following structure:

[cyclohexene structure with substituents: —CH$_2$—CH, HC, HC, HC, (CH$_2$)$_4$CH$_3$, HC—(CH$_2$)$_7$CH$_2$—, (CH$_2$)$_4$CH$_3$]

or

[cyclohexane structure with substituents: —CH$_2$—CH, H$_2$C, H$_2$C, HC, (CH$_2$)$_4$CH$_3$, HC—(CH$_2$)$_7$CH$_2$—, (CH$_2$)$_4$CH$_3$]

and mixtures thereof;

n is an integer ranging from 0 to 9.

x is an integer ranging from 1 to 10.

PREFERRED EMBODIMENT

In a preferred embodiment a is 1.
In a more preferred embodiment a is 10
In a more preferred embodiment $R^1$ is an alkyl having 18 carbons.
In a more preferred embodiment $R^3$ is derived from dimer acid.
In a more preferred embodiment $R^2$ is an alkyl having 18 carbons.
In a more preferred embodiment $R^3$ is an alkyl having 7 carbons.
In a more preferred embodiment n is 2.
In a more preferred embodiment n is 0.
In a more preferred embodiment x is 1.

Raw Materials

Fatty Acids

Fatty acids useful in the practice of the present invention are items of commerce commercially available from Cognis.

Fatty Acid Names

Fatty acids useful as raw materials in the preparation of compounds of the present invention are commercially available from a variety of sources including Procter and Gamble of Cincinnati Ohio. The structures are well known to those skilled in the art.

$$R-C(O)-OH$$

Saturated

| Example | R Formula | Common Name | Molecular Weight |
|---|---|---|---|
| 1 | $C_7H_5$ | Caprylic | 144 |
| 2 | $C_9H_9$ | Capric | 172 |
| 3 | $C_{11}H_{23}$ | Lauric | 200 |
| 4 | $C_{13}H_{27}$ | Myristic | 228 |
| 5 | $C_{14}H_{29}$ | Pentadecanoic | 242 |
| 6 | $C_{15}H_{31}$ | Palmitic | 256 |

Saturated

| Example | R Formula | Common Name | Molecular Weight |
|---|---|---|---|
| 7 | $C_{17}H_{35}$ | Stearic | 284 |
| 8 | $C_{17}H_{35}$ | Isosteric | 284 |
| 9 | $C_{19}H_{39}$ | Arachidinic | 312 |
| 10 | $C_{21}H_{43}$ | Behenic | 340 |
| 12 | $C_{26}H_{53}$ | cetrotic | 396 |
| 13 | $C_{33}H_{67}$ | geddic acid | 508 |

Unsaturated

| Example | R Formula | Common Name | Molecular Weight |
|---|---|---|---|
| 14 | $C_{17}H_{33}$ | Oleic | 282 |
| 15 | $C_{17}H_{31}$ | Linoleic | 280 |
| 16 | $C_{17}H_{29}$ | Linolenic | 278 |
| 17 | $C_{15}H_{29}$ | Palmitoleic | 254 |
| 18 | $C_{13}H_{25}$ | Myristicoleic | 226 |
| 19 | $C_{21}H_{41}$ | Erucic | 338 |

Polyglycerol

Polyglycerol is useful as raw materials in the preparation of compounds of the present invention. Polyglycerols are commercially available from a variety of sources including Solvay Chemicals of Rheinberg Germany.

The structures are well known to those skilled in the art.

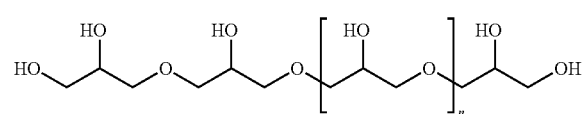

wherein;
n is an integer ranging from 0 to 9.

| Example | n | MW |
|---|---|---|
| 20 | 0 | 225.0 |
| 21 | 3 | 450.0 |
| 22 | 7 | 750.0 |

Example 23

Dimer Acid

Dimer acid is an item of commerce available commercially from Cognis Corporation. It conforms to the following structure:

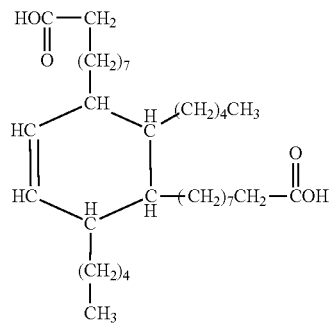

Example 24

Hydrogenated Dimer Acid

Hydrogenated dimer acid is an item of commerce available commercially from Henkel Corporation. It conforms to the following structure:

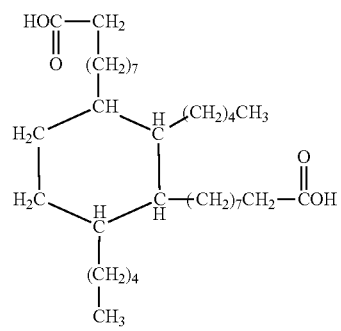

Dicarboxylic Acid

Dicarboxylic acid useful as raw materials in the synthesis of the compounds of the present invention are commercially available from a variety of sources including Cognis. They conform to the following structure;

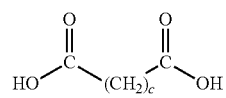

wherein;
c is an integer ranging from 1 to 10.

Saturated Dicarboxylic Acids

| Saturated Dicarboxylic acids | | | |
|---|---|---|---|
| Example | Common Name | c | Molecular Weight |
| 25 | Malonic | 1 | 104 |
| 26 | Succinic | 2 | 118 |
| 27 | Glutaric | 3 | 132 |
| 28 | Adipic | 4 | 146 |
| 29 | Pimelic | 5 | 160 |
| 30 | Subric | 6 | 174 |

-continued

Saturated Dicarboxylic acids

| Example | Common Name | c | Molecular Weight |
|---|---|---|---|
| 31 | Azelaic | 7 | 188 |
| 32 | Sebacic | 8 | 202 |
| 33 | Undecanedioic | 9 | 216 |
| 34 | Dodecanedioic | 10 | 230 |

Monofunctional Silicone Compounds

Monofunctional silicone polymers useful in the synthesis of the compounds of the present invention available from Siltech LLC conforming to the following structure:

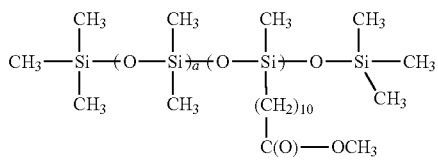

a is an integer ranging from 1 to 20.

These products are the result of hydrosilylation of a silanic hydrogen containing polymer with methyl undecylenate.

| | Silicone Capping Agents | |
|---|---|---|
| Example | "a" Value | Molecular Weight |
| 32 | 1 | 420 |
| 33 | 5 | 1444 |
| 34 | 10 | 2724 |
| 35 | 20 | 5284 |

General Procedure

A specified number of grams polyglycerol (examples 20-22) is added to a specified amount of fatty acids (examples 1-18), the specified number of grams of the specified diacid (examples 23 and 34) and the specified number of grams of the specified silicone capping agent (examples 32-35). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

The compounds of the present invention having a terminal silicone cap have low surface tensions and provide outstanding spreadability on the skin. This makes them very desirable for use in the personal care market.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein above but rather that the claims be construed as encompassing all the features of patentable novelty which reside in the present invention, including all features which would be treated as equivalents thereof by those skilled in the art to which the invention pertains.

The invention claimed is:

1. A terminal silicone polyester having the following structure:

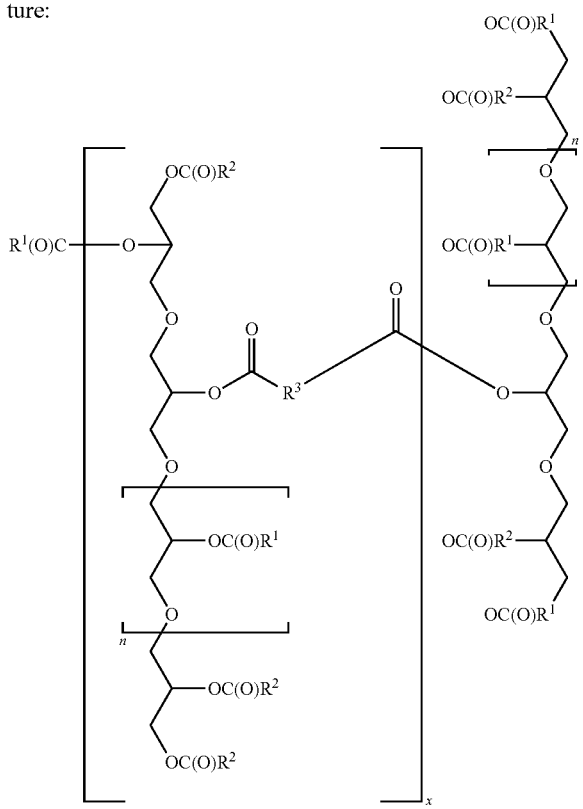

| | Polyglycerol | | $R^1$ | | $R^2$ | | Diacid | |
|---|---|---|---|---|---|---|---|---|
| Example | Example | Grams | Example | Grams | Example | Grams | Example | Grams |
| 35 | 20 | 100.0 | 32 | 100.0 | 32 | 28.7 | 24 | 21.4 |
| 36 | 20 | 86.8 | 32 | 86.8 | 32 | 54.1 | 24 | 22.2 |
| 37 | 21 | 188.4 | 33 | 22.4 | 2 | 15.7 | 25 | 23.5 |
| 38 | 21 | 172.6 | 33 | 20.6 | 2 | 31.2 | 25 | 25.7 |
| 39 | 22 | 204.4 | 34 | 21.3 | 7 | 1.8 | 26 | 22.5 |
| 40 | 22 | 199.2 | 34 | 20.8 | 7 | 3.8 | 26 | 26.2 |
| 41 | 20 | 230.2 | 35 | 12.4 | 8 | 2.8 | 28 | 4.7 |
| 42 | 20 | 232.3 | 35 | 12.5 | 8 | 1.3 | 28 | 4.0 |
| 43 | 21 | 107.4 | 32 | 86.9 | 10 | 9.6 | 31 | 46.0 |
| 44 | 21 | 99.3 | 32 | 80.4 | 10 | 19.3 | 31 | 50.9 |
| 45 | 22 | 168.2 | 33 | 32.8 | 14 | 14.0 | 24 | 34.9 |
| 46 | 22 | 153.9 | 33 | 30.0 | 14 | 27.9 | 24 | 38.2 | wherein,
R¹ is

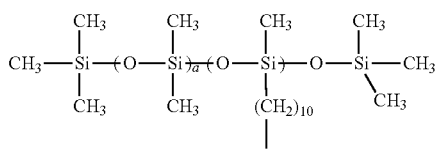

a is an integer ranging from 1 to 20;
R² is selected from the group consisting of

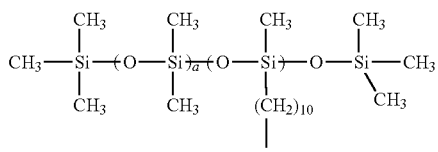

a is an integer ranging from 1 to 20;
and alkyl containing 8 to 26 carbons or mixtures thereof;
R³ is independently selected from the group consisting of alkyl having 2 to 12 carbons, alkyl having the following structure:

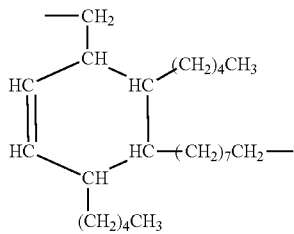

or

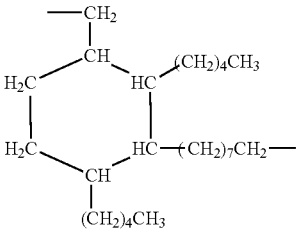

and mixtures thereof;
n is an integer ranging from 0 to 9,
x is an integer ranging from 1 to 10.

2. A terminal silicone polyester of claim 1 wherein a is 1.

3. A terminal silicone polyester of claim 1 wherein a is 10.

4. A terminal silicone polyester of claim 1 wherein a is 20.

5. A terminal silicone polyester of claim 1 wherein R¹ is an alkyl having 18 carbons.

6. A terminal silicone polyester of claim 1 wherein R³ is derived from dimer acid.

7. A terminal silicone polyester of claim 1 wherein R³ is derived from hydrogenated dimer acid.

8. A terminal silicone polyester of claim 1 wherein R² is an alkyl having 18 carbons.

9. A terminal silicone polyester of claim 1 wherein R³ is an alkyl having 7 carbons.

10. A terminal silicone polyester of claim 1 wherein n is 2.

11. A terminal silicone polyester of claim 1 wherein n is 0.

* * * * *